United States Patent [19]
Dotson et al.

[11] Patent Number: 6,121,332
[45] Date of Patent: Sep. 19, 2000

[54] MONOBENZYLIDENE SORBITOL GELLING AGENT AND METHOD OF USE THEREOF

[75] Inventors: Darin L. Dotson, Spartanburg; Walter A. Scrivens, Newberry, both of S.C.

[73] Assignee: Milliken & Company, Spartanburg, S.C.

[21] Appl. No.: 09/322,754

[22] Filed: May 28, 1999

[51] Int. Cl.[7] .......................... B01J 13/00; C07C 43/307
[52] U.S. Cl. .......................... 516/105; 514/944; 568/592
[58] Field of Search .......................... 516/105; 514/944; 549/356, 510; 568/592

[56] References Cited

U.S. PATENT DOCUMENTS

| | | | |
|---|---|---|---|
| 3,630,896 | 12/1971 | Oka et al. | 514/944 X |
| 4,267,110 | 5/1981 | Uchiyama | 260/340.7 |
| 4,781,917 | 11/1988 | Luebbe et al. | 514/944 X |
| 4,829,108 | 5/1989 | Okuda et al. | 524/37 |
| 5,547,577 | 8/1996 | Vogler et al. | 516/105 X |
| 5,731,474 | 3/1998 | Scrivens et al. | 568/592 |
| 5,964,691 | 10/1999 | Mehl | 516/105 X |

*Primary Examiner*—Richard D. Lovering
*Attorney, Agent, or Firm*—Terry T. Moyer; William S. Parks

[57] ABSTRACT

This invention relates to gelled compositions formed through the introduction of specific solvents to compositions comprising 2,4-O-(3,4-dimethylbenzylidene)-D-sorbitol. Such compositions provide excellent gelling for any number of potential applications, particularly where translucent gels are desired. In general, these compositions are formed by introducing heated solvents to the specific monobenzylidene sorbitol present in its solid form. The monobenzylidene sorbitol is preferably added in very low amounts to the target solvents in order to generate the desired gelling effect. A method of producing such gelled compositions is also provided.

17 Claims, No Drawings

6,121,332

MONOBENZYLIDENE SORBITOL GELLING AGENT AND METHOD OF USE THEREOF

FIELD OF THE INVENTION

This invention relates to gelled compositions formed through the introduction of specific solvents to compositions comprising 2,4-O-(3,4-dimethylbenzylidene)-D-sorbitol. Such compositions provide excellent gelling for any number of potential applications, particularly where translucent gels are desired. In general, these compositions are formed by introducing heated solvents to the specific monobenzylidene sorbitol present in its solid form. The monobenzylidene sorbitol is preferably added in very low amounts to the target solvents in order to generate the desired gelling effect. A method of producing such gelled compositions is also provided.

BACKGROUND OF THE PRIOR ART

Monobenzylidene sorbitols ("MBS"), also known as monobenzylidene sorbitol acetals, have found utility as gelling agents in the past for coating compositions. For example, U.S. Pat. No. 4,829,108 to Okuda et al., teaches p-methylbenzylidene sorbitol and other monosubstituted compounds for gelling. Such compounds are produced through the reaction of sorbitol and a monosubstituted aromatic aldehyde. Other monobenzylidene sorbitols, unsubstituted, are taught within U.S. Pat. No. 4,267,110 to Uchiyama et al. Patentee, however, makes no mention of the potential gelling characteristics of such unsubstituted compounds. Although Okuda et al. teach the possible utilization of monosubstituted monobenzylidene sorbitols as gelling agents, there is no discussion of the potential use of these compounds as gelling agents within different types of solvents and for other potential uses other than coatings. Thus, there is a need, which has been unmet within the gelling composition field, to provide a simple method for forming a gel composition which can be utilized with various and different solvents, particularly with very low amounts of gelling agent. To date, it is believed that there are no teachings or fair suggestions of utilizing 2,4-O-(3,4-dimethylbenzylidene)-D-sorbitol in combination with a heated solvent, such as water, glycerine, mineral oil, or mixtures thereof, to provide an effective gelling composition. The relative cost of producing such gel compositions is quite low since the amount of potentially expensive monobenzylidene sorbitol is minimal, although the resultant gel composition performs extremely well.

OBJECTS OF THE INVENTION

Therefore, an object of the invention is to provide a gelled composition for use in any number of applications, such as cosmetic sticks, lotions, and the like, which is produced through the introduction of a very low amount of monobenzylidene sorbitol and a readily available solvent. A further object of the invention is to provide a simple method for providing such desired gelling compositions and characteristics comprising heating the target solvent and introducing such within a monobenzylidene sorbitol-containing composition. Another object of the invention is to provide a relatively inexpensive gelling method for easy incorporation within commercial products and processes. Additionally, it is an object of this invention to provide a gelling composition and method which provides long-term storage-stable gels.

DETAILED DESCRIPTION OF THE INVENTION

The inventive composition is formed by the introduction of a composition comprising a specific type or types of solvent into a composition comprising 2,4-O-(3,4-dimethylbenzylidene)-D-sorbitol. Such a specific monobenzylidene sorbitol surprisingly provides gelling characteristics when mixed with various and different solvents, including water, glycerine, mineral oils, and any mixtures thereof. In actuality, these components of the target gel compositions do not react with one another; the monobenzylidene sorbitol appears to form a network (or net-like) structure within the solvent to encompass the solvent and hold it in place in a gelled state. Upon mixing of the two components, wherein the solvent is heated to an elevated temperature of at most its boiling point, the mixture is stirred and allowed to cool. It has been theorized and observed that the more pure the 2,4-O-(3,4-dimethyl-benzylidene)-D-sorbitol sample, coupled with the longer cooling time needed to permit gelation of the target composition (such as by the larger container in which the mixture is placed), the clearer the resultant gel composition. In contrast, but still within the scope of this invention, minor impurities or shorter cooling times provide more translucent and less transparent gel compositions upon gelation of the target composition. Again, surprisingly, it has been found that extremely low amounts of the 2,4-O-(3,4-dimethylbenzylidene)-D-sorbitol in relation to the solvent provides extremely effective gelation for the overall target composition. For example, from about 0.01 to about 3 weight percent of the total amount of 2,4-O-(3,4-dimethylbenzylidene)-D-sorbitol and solvent results in a gelled composition exhibiting the desired hardness and translucence. Furthermore, preferable amounts of the monobenzylidene sorbitol are from about 0.1 to 2 weight percent; more preferably from about 0.5 to 1.5 weight percent; and most preferably at about 1 weight percent are utilized to provide optimum hardness, translucence; and even transparency.

Also contemplated within this invention is a method of gelling a solvent selected from the group consisting of water, glycerine, mineral oil, and any mixtures thereof, wherein said solvent is either present alone or within a composition comprising other materials, comprising the process steps of:

(a) providing a composition comprising the solvent listed above;

(b) providing a composition comprising 2,4-O-(3,4-dimethylbenzylidene)-D-sorbitol;

(c) heating the composition from step "a" to at most its boiling temperature;

(d) contacting the heated composition from step "c" with the composition of step "b" with stirring, wherein the composition of step "b" is present in an amount of from about 0.01 to about 3 weight percent of the total weight of the compositions of step "a" and "b";

(e) allowing sufficient time for the resultant composition of step "d" to cool and subsequently gel.

The same range of proportions of the 2,4-O-(3,4-dimethylbenzylidene)-D-sorbitol are utilized within the method as noted above. The temperature ranges utilized are highly dependent upon the type of solvent utilized. For instance, water has a boiling point of about 100° C., which is thus the high temperature utilized (as could be adjusted for air pressure, and the like, depending on geographic location or other reason). Thus, water can be introduced to the monobenzylidene sorbitol composition from about 50° C. to its boiling point; preferably from about 750 to 95° C.; and most preferably from about 800 to 90° C. For glycerine, the temperature ranges should be from about from about 60° C. to about 130° C. (again depending upon air pressure, and the like); preferably from about 750 to 125° C.; more preferably from about 100° C. to about 120° C.; and most preferably at about 120° C. For mineral oil, 70° C. to about 140° C. (again depending upon air pressure, and the like); preferably from about 90° to 135° C.; more preferably from about 110° C. to about 130° C.; and most preferably at about 130° C.

The specific monobenzylidene sorbitol of this invention, 2,4-O-(3,4-dimethylbenzylidene)-D-sorbitol, is generally produced through the reaction of equivalent molar amounts of powdered D-sorbitol and 3,4-dimethylbenzaldehyde. For example, one particular method follwed entailed mixing together in a reaction vessel, the two above-listed reactants in equal 250 mmol amounts, 2.5 g water, 375 mL cyclohexane, 15 mL dimethylformamide, and 1 g concentrated sulfuric acid. Nitrogen was added to this reaction to replace the air, while stirring. After heating and refluxing in an oil bath, a homogeneous mixture was produced. Eventually, certain amounts of cyclohexane and water were removed and fresh amounts of cyclohexane were added. Upon further heating of the remaining mixture (about 5 more hours at about 77.9° C.), the mixture was then allowed to cool. The cooled mixture was then neutralized with sodium carbonate and water was added to the resulting slurry. The aqueous filtrate of the slurry was then evaporated under reduced pressure to produce a translucent jelly. This gelatinous solid was then evaporated under vacuum to produce a white solid. Such a solid product was analyzed by $H^1$ and $C^{13}$ NMR (with deuterated DMSO) to be 2,4-O-(3, 4-dimethylbenzylidene)-D-sorbitol. It is noted that some lower amounts of the related dibenzylidene sorbitol are also formed by this process, thus, it is commercially and practically unfeasable to utilize this method to produce such dibenzylidene compounds.

This method gives a very pure sample (approaching 100% pure) of the target compound; however, some impurities may be formed in other procedures [impurities such as 1,3-O-(3,4-dimethylbenzylidene)-D-sorbitol]. Such impurities are thus contemplated as potential components within the inventive compositions and methods. As noted above, such impurities may provide more opaque, at least less transparent, resultant gel compositions. Thus, theoretically, the purer the monobenzylidene sorbitol, the better.

The gel composition preferably comprises only the sorbitol compound and the solvent. However, there are other compositions in which this composition may be added to improve the gelling characteristics or to provide such gelation. For instance, deodorant sticks, and other cosmetic types of articles or compositions, would include other materials, such as perfumes, odor-destroying compounds, and the like. Thus, other materials or additives may be present and may include plasticizers, antistatic agents, stabilizers, ultraviolet absorbers, antioxidants, antistatic compounds, chlorine scavengers, and the like.

Preferred Embodiments of the Invention

Examples of particularly preferred gel compositions and methods of forming such within the scope of the present invention are presented below.

EXAMPLE 1

1.0 g of 2,4-O-(3,4-dimethylbenzylidene)-D-sorbitol, being in crystalline form, was mixed with 50 g of water heated to above about 90° C. until a homogeneous mixture was obtained. The hot solution was then poured into a gel-stick container and allowed to cool for three hours at room temperature. A completely clear, resilient gel formed which was also thixotropic in nature. Some weeping (water appearing on the surface) was observed. The gel has not come out of its like gel-like state.

EXAMPLE 2

1.0 g of 2,4-O-(3,4-dimethylbenzylidene)-D-sorbitol, being in crystalline form, was mixed with 50 g of glycerine (glycerol) heated to above about 120° C. until a homogeneous mixture was obtained. The hot solution was then poured into a gel-stick container and allowed to cool for three hours at room temperature. A translucent, resilient, firm gel formed. The gel has not come out of its like gel-like state.

EXAMPLE 3

1.5 g of 2,4-O-(3,4-dimethylbenzylidene)-D-sorbitol, being in crystalline form, was mixed with 50 g of glycerine (glycerol) heated to above about 120° C. until a homogeneous mixture was obtained. The hot solution was then poured into a gel-stick container and allowed to cool for three hours at room temperature. A translucent, hard, resilient gel formed. The gel has not come out of its like gel-like state.

EXAMPLE 4

1.0 g of 2,4-O-(3,4-dimethylbenzylidene)-D-sorbitol, being in crystalline form, was mixed with 50 g of mineral oil heated to above about 130° C. until a homogeneous mixture was obtained. The hot solution was then poured into a gel-stick container and allowed to cool for three hours at room temperature. A clear, weak, but resilient gel formed. The gel has not come out of its like gel-like state.

EXAMPLE 5

1.5 g of 2,4-O-(3,4-dimethylbenzylidene)-D-sorbitol, being in crystalline form, was mixed with 50 g of mineral oil heated to above about 130° C. until a homogeneous mixture was obtained. The hot solution was then poured into a gel-stick container and allowed to cool for three hours at room temperature. A clear, weak, but resilient gel formed. The gel has not come out of its like gel-like state.

EXAMPLE 6 (Comparative)

2.0 g of 2,4-O-(3,4-dimethylbenzylidene)-D-sorbitol, being in crystalline form, was mixed with 50 g of mineral oil heated to above about 130° C. The sorbitol was insoluble in the mineral oil at this concentration so no gel was formed.

EXAMPLE 7 (Comparative)

1.0 g of 2,4-O-(3,4-dimethylbenzylidene)-D-sorbitol, being in crystalline form, was mixed with 50 g of propylene glycol oil heated to above about 110° C. until a homogeneous mixture was obtained. The hot solution was then poured into a gel-stick container and allowed to cool for three hours at room temperature. An opaque, weak, gel-like substance formed.

EXAMPLE 8 (Comparative)

1.5 g of 2,4-O-(3,4-dimethylbenzylidene)-D-sorbitol, being in crystalline form, was mixed with 50 g of propylene glycol heated to above about 110° C. until a homogeneous mixture was obtained. The hot solution was then poured into a gel-stick container and allowed to cool for three hours at room temperature. An opaque, weak gel-like substance formed.

Having described the invention in detail it is obvious that one skilled in the art will be able to make variations and modifications thereto without departing from the scope of the present invention. Accordingly, the scope of the present invention should be determined only by the claims appended hereto.

That which is claimed is:

1. A gelled composition produced by mixing 2,4-O-(3,4-dimethylbenzylidene)-D-sorbitol and a heated solvent selected from the group consisting of water, glycerine, mineral oil, and any mixtures thereof.

2. The composition of claim 1 wherein the 2,4-O-(3,4-dimethylbenzylidene)-D-sorbitol is added in an amount of from about 0.01 to about 3 weight percent of the total weight of the solvent and the 2,4-O-(3,4-dimethylbenzylidene)-D-sorbitol.

3. The composition of claim 2 wherein the 2,4-O-(3,4-dimethylbenzylidene)-D-sorbitol is added in an amount of from about 0.5 to about 1.5 weight percent of the total weight of the solvent and the 2,4-O-(3,4-dimethylbenzylidene)-D-sorbitol.

4. The composition of claim 1 wherein the 2,4-O-(3,4-dimethylbenzylidene)-D-sorbitol is added in an amount of from about 0.1 to about 2 weight percent of the total weight of the solvent and the 2,4-O-(3,4-dimethylbenzylidene)-D-sorbitol.

5. The composition of claim 4 wherein the 2,4-O-(3,4-dimethylbenzylidene)-D-sorbitol is added in an amount of about 1 weight percent of the total composition.

6. A method of gelling a solvent selected from the group consisting of water, glycerine, mineral oil, and any mixtures thereof, wherein said solvent is either present alone or within a composition comprising other materials, comprising the process steps of:

(a) providing a composition comprising the solvent listed above;

(b) providing a composition comprising 2,4-O-(3,4-dimethylbenzylidene)-D-sorbitol;

(c) heating the composition from step "a" to at most its boiling temperature;

(d) contacting the heated composition from step "c" with the composition of step "b" with stirring, wherein the composition of step "b" is present in an amount of from about 0.01 to about 3 weight percent of the total weight of the compositions of step "a" and "b"; and (e) allowing sufficient time for the resultant composition of step "d" to cool and subsequently gel.

7. The method of claim 6 wherein said solvent is water and the temperature of step "c" is from about 50° to about 100° C.

8. The method of claim 7 wherein said solvent is water and the temperature of step "c" is from about 80° to about 90° C.

9. The method of claim 6 wherein said solvent is water and the temperature of step "c" is from about 75° to about 95° C.

10. The method of claim 6 wherein said solvent is glycerine and the temperature of step "c" is from about 60° to about 130° C.

11. The method of claim 10 wherein said solvent is glycerine and the temperature of step "c" is from about 75° to about 125° C.

12. The method of claim 11 wherein said solvent is glycerine and the temperature of step "c" is about 120° C.

13. The method of claim 11 wherein said solvent is glycerine and the temperature of step "c" is from about 100° to about 120° C.

14. The method of claim 6 wherein said solvent is mineral oil and the temperature of step "c" is from about 70° to about 140° C.

15. The method of claim 14 wherein said solvent is mineral oil and the temperature of step "c" is from about 90° to about 135° C.

16. The method of claim 15 wherein said solvent is mineral oil and the temperature of step "c" is about 30° C.

17. The method of claim 12 wherein said solvent is glycerine and the temperature of step "c" is from about 110° to about 130° C.

* * * * *

UNITED STATES PATENT AND TRADEMARK OFFICE
CERTIFICATE OF CORRECTION

PATENT NO.   : 6,121,332
DATED        : September 19, 2000
INVENTOR(S)  : Darin L. Dotson and Walter A. Scrivens It is certified that error appears in the above-identified patent and that said Letters Patent is hereby corrected as shown below:

<u>Column 6,</u>
Line 36, after the word "about" delete "30" and insert -- 130 --.

Signed and Sealed this

Fifteenth Day of July, 2003

JAMES E. ROGAN
*Director of the United States Patent and Trademark Office*